United States Patent
Matsubara

(10) Patent No.: US 12,205,708 B2
(45) Date of Patent: Jan. 21, 2025

(54) MEDICAL IMAGE PROCESSING APPARATUS AND METHOD

(71) Applicant: CANON MEDICAL SYSTEMS CORPORATION, Otawara (JP)

(72) Inventor: Ryota Matsubara, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 370 days.

(21) Appl. No.: 17/327,961

(22) Filed: May 24, 2021

(65) Prior Publication Data

US 2021/0375436 A1    Dec. 2, 2021

(30) Foreign Application Priority Data

May 29, 2020  (JP) ................. 2020-094851

(51) Int. Cl.
*G16H 30/40* (2018.01)
*G06T 7/00* (2017.01)
*G06T 7/11* (2017.01)

(52) U.S. Cl.
CPC .......... *G16H 30/40* (2018.01); *G06T 7/0014* (2013.01); *G06T 7/11* (2017.01); *G06T 2207/20021* (2013.01); *G06T 2207/30016* (2013.01)

(58) Field of Classification Search
CPC ......... G16H 30/40; G06T 7/11; G06T 7/0014; G06T 2207/20021; G06T 2207/30016; G06T 7/0012; G06T 2210/41; G06T 2207/30101

See application file for complete search history.

(56) References Cited

U.S. PATENT DOCUMENTS

| | | | |
|---|---|---|---|
| 8,023,709 B2* | 9/2011 | Joshi ................ | G06V 10/267 382/130 |
| 10,898,152 B1* | 1/2021 | Kim .................. | G06T 7/11 |
| 2015/0043774 A1* | 2/2015 | Harder ............... | G06V 10/141 382/128 |
| 2016/0070360 A1* | 3/2016 | Chehade ............. | G06V 40/20 345/156 |

(Continued)

FOREIGN PATENT DOCUMENTS

| | | |
|---|---|---|
| JP | 2008-188428 A | 8/2008 |
| JP | 2011-24620 A | 2/2011 |

OTHER PUBLICATIONS

Takemura, et al. "Usefulness of the classification technique of cerebral artery for 2D/3D registration", Japanese Journal of Medical Physics. vol. 27, No. 1. 2007, 11 pages (with English Abstract).

(Continued)

*Primary Examiner* — Bobbak Safaipour
*Assistant Examiner* — Ashley L. Hytrek
(74) *Attorney, Agent, or Firm* — Oblon, McClelland, Maier & Neustadt, L.L.P.

(57) ABSTRACT

A medical image processing apparatus includes processing circuitry configured to acquire medical image data representing a region including a target site, divide the medical image data into a plurality of pieces of divisional data according to an anatomical structure, extract a target region corresponding to the target site from each of the pieces of divisional data according to a particular condition, and cause an output circuit to output information on the extracted target region.

19 Claims, 7 Drawing Sheets

(56) References Cited

U.S. PATENT DOCUMENTS

2022/0115136 A1\* 4/2022 Fuchigami ............... G06N 3/08
2023/0079772 A1\* 3/2023 Moriconi ............. G06T 7/0012
　　　　　　　　　　　　　　　　　　　　　382/128

OTHER PUBLICATIONS

Japanese Office Action issued Oct. 31, 2023 in Japanese Patent Application No. 2020-094851, 2 pages.

\* cited by examiner

MEDICAL IMAGE PROCESSING APPARATUS AND METHOD

CROSS-REFERENCE TO RELATED APPLICATION

This application is based upon and claims the benefit of priority from Japanese Patent Application No. 2020-094851, filed on May 29, 2020; the entire contents of which are incorporated herein by reference.

FIELD

Embodiments described herein relate generally to a medical image processing apparatus and a medical image processing method.

BACKGROUND

In medical image diagnosis, internal organs, blood vessels, bones, or other structures appearing on medical images are subjected to segmentation or region extraction. Through segmentation, a region corresponding to a target site can be isolated from the other regions, for example. Examples of the segmentation includes various methods such as template matching, threshold processing using pixel values, and else.

Meanwhile, a site or region having an anomalous structure is subjected to segmentation in some cases. It may be difficult to properly extract such a site by the conventional segmentation. The circle of Willis is, for example, a known peculiar structure in the cerebral arteries. The circle of Willis refers to a circular or hexagonal anastomosis formed by connection of cerebral arteries. Conventionally, to automatically segment the circle of Willis from an arterial mask, which is created from a contrast image, the anomalous structure is subjected to hexagonal template matching.

The circle of Willis, however, varies in terms of morphology and is hypoplastic in some people. Simple template matching is thus not sufficient to deal with various shapes of the circle of Willis. In addition, presence of an occlusion in the artery caused by a blood clot, if it occurs, prevents identification of structures located farther than the occlusion on the arterial mask. Thus, template matching is not applicable to such a case.

DETAILED DESCRIPTION

According to one embodiment, in general, a medical image processing apparatus includes processing circuitry configured to acquire medical image data representing a region including a target site, divide the medical image data into a plurality of pieces of divisional data according to an anatomical structure, extract a target region corresponding to the target site from each of the pieces of divisional data according to a particular condition, and cause an output circuit to output information on the extracted target region.

Hereinafter, a medical image processing apparatus and a medical image processing method according to an embodiment will be described with reference to the accompanying drawings.

Figure 1:
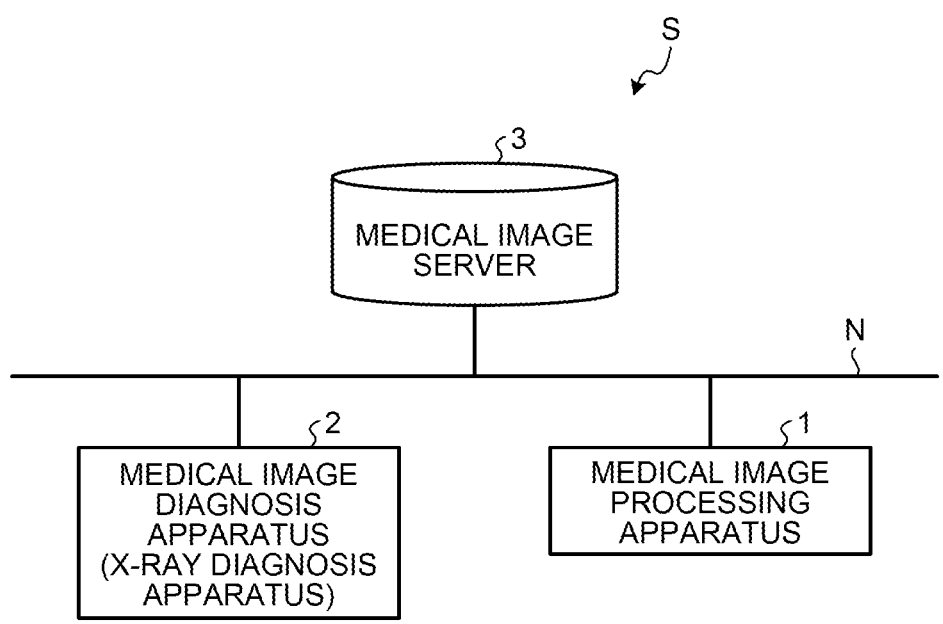
FIG. 1 illustrates a medical information processing system including a medical image processing apparatus, a medical image diagnosis apparatus, and a medical image server according to one embodiment.

FIG. 1 illustrates a medical information processing system S including a medical image processing apparatus 1, a medical image diagnosis apparatus 2, and a medical image server 3 according to one embodiment. The medical image processing apparatus 1, the medical image diagnosis apparatus 2, and the medical image server 3 are mutually communicable via a network N. The medical image processing apparatus 1 and the medical image server 3 can be installed not only in a hospital and but also in a facility outside a hospital or in the cloud.

The medical image processing apparatus 1 is exemplified by a numerical computing apparatus, such as a personal computer or a medical work station. The medical image processing apparatus 1 performs medical information processing to medical images captured by the medical image diagnosis apparatus 2. For example, the medical image processing apparatus 1 extracts a target site from a medical image captured by the medical image diagnosis apparatus 2 (hereinafter, referred to as target site extraction). The target site extraction to be executed by the medical image processing apparatus 1 will be described later in detail.

In the present embodiment the circle of Willis will be an exemplary target site for the sake of concrete explanation. The circle of Willis is also referred to as the cerebral arterial circle, and it is a ring-form arterial anastomosis formed by the internal carotid arteries, the vertebral arteries, and their branches in the cerebral base.

Figure 2:
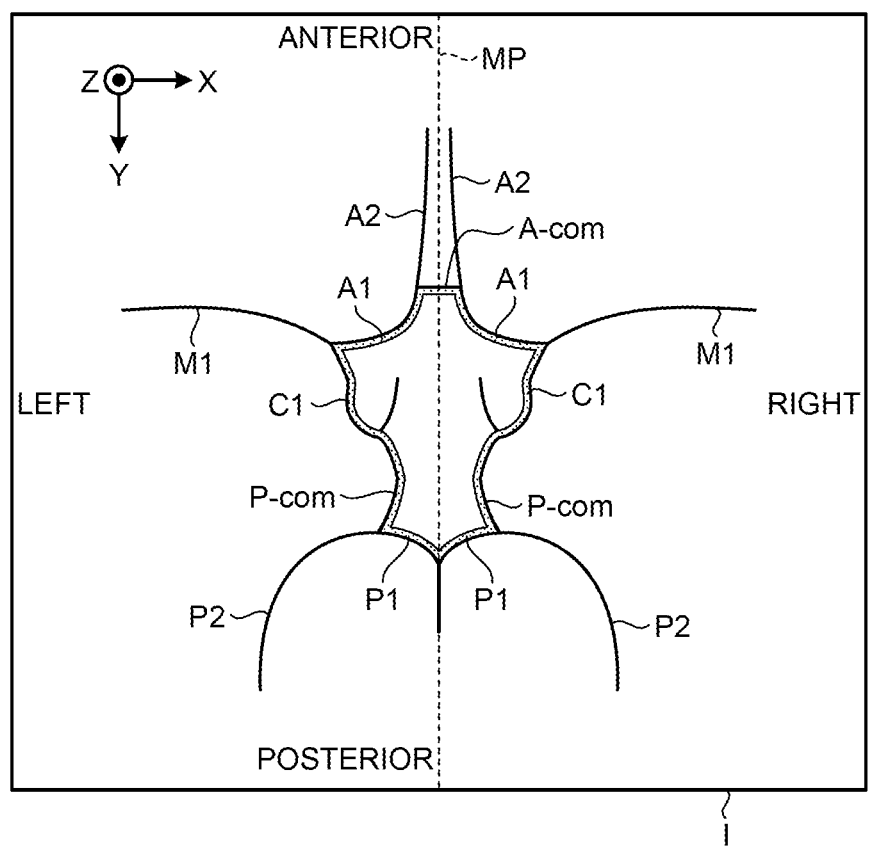
FIG. 2 is a partial schematic view of cerebral arteries including the circle of Willis, as viewed from above the head.

FIG. 2 is a partial schematic view of the cerebral arteries including the circle of Willis, as viewed from above the head. FIG. 2 depicts a cerebral artery mask image I showing the cerebral arteries as a region of interest, created by subtraction from contrast image data and non-contrast image data of the brain, for example.

In FIG. 2, Z-axis direction, Y-axis direction, and X-axis direction are defined, corresponding to direction of body axis, anteroposterior direction, and transverse direction, respectively. That is, a positive direction of Z-axis direction corresponds to a direction from the head to the feet of the human body. A positive direction of Y-axis direction corresponds to a direction from the front side to the back side of the human body. A positive direction of X-axis direction corresponds to a direction from the left side to the right side of the human body.

As illustrated in FIG. 2, the cerebral arteries are divisible into a right side and a left side with respect to a reference plane MP. In the present embodiment the reference plane MP is defined as a median plane. Herein, the median plane refers to a plane orthogonal to the body axis separating the right side and left side of the brain. The median plane can be calculated from a result of segmentation of the brain region.

Part of the cerebral arteries illustrated in FIG. 2 includes left and right A1 segments, left and right segments A2, left and right segments M1, left and right C1 segments, left and right P1 segments, left and right P2 segments, the anterior communicating artery A-com, and the posterior communicating arteries P-corn. The circle of Willis includes the left and right A1 segments, the anterior communicating artery A-corn, the posterior communicating arteries P-corn, the left and right C1 segments, and the left and right P1 segments. In FIG. 2 the region corresponding to the circle of Willis is indicated by the double line.

Referring back to FIG. 1, the medical image diagnosis apparatus 2 images a subject to capture a medical image of the subject. In the present embodiment the medical image diagnosis apparatus 2 represents a cardiovascular X-ray diagnosis apparatus (angiography) by way of example.

The medical image server 3 serves as a database for storing and managing, for each patient, image data captured by the medical image diagnosis apparatus 2 and information associated with the image data. According to the present embodiment, the medical image server 3 includes a database for a hospital information system (HIS) or a radiology information system (RIS), for example.

Figure 3:
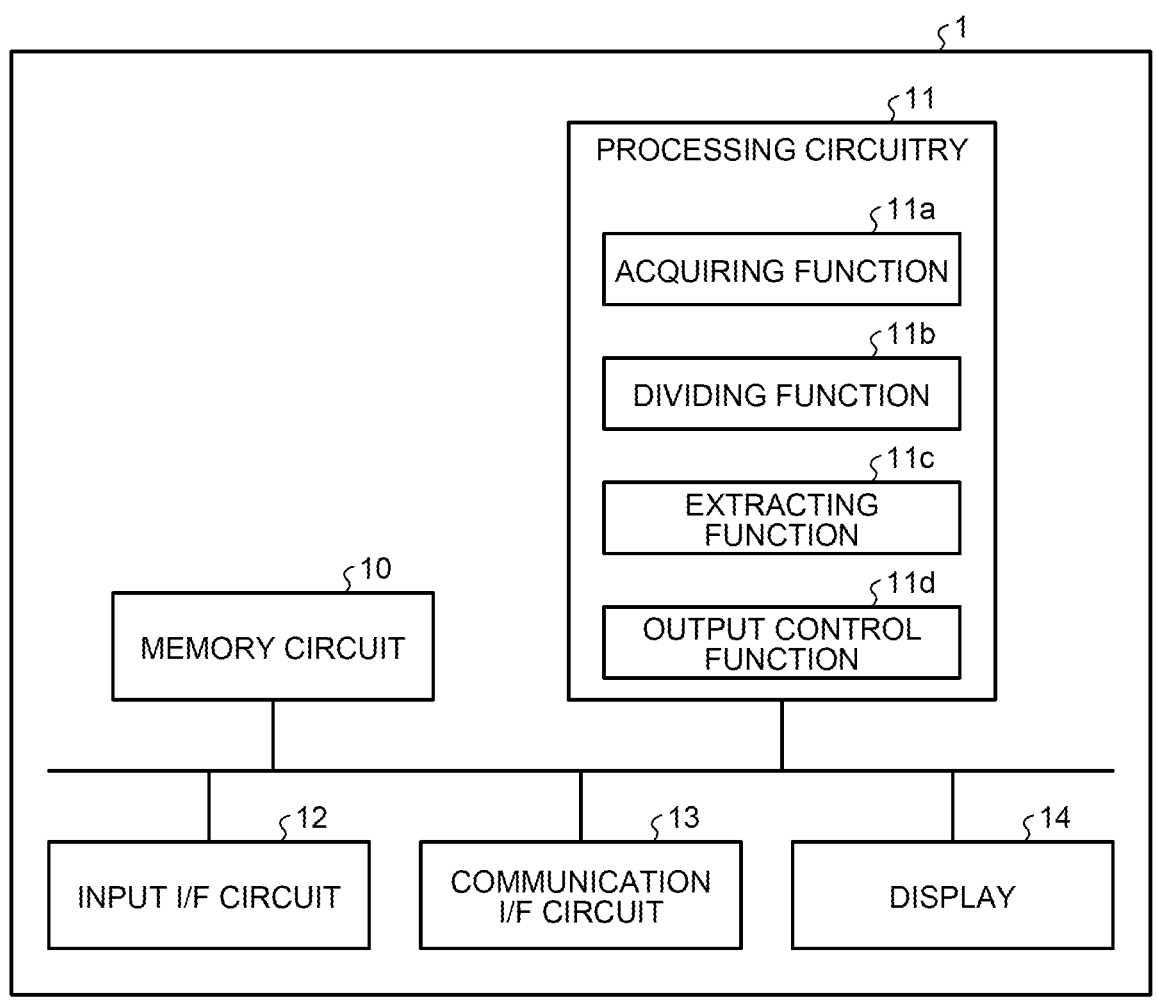
FIG. 3 is a block diagram of an exemplary configuration of the medical image processing apparatus of the embodiment.

FIG. 3 illustrates an exemplary configuration of the medical image processing apparatus 1 of the present embodiment. As illustrated in FIG. 3, the medical image processing apparatus 1 includes a memory circuit 10, processing circuitry 11, an input interface (I/F) circuit 12, a communication interface (I/F) circuit 13, and a display 14.

The memory circuit 10 includes semiconductor memory elements such as a random access memory (RAM) and a flash memory, a hard disk, an optical disk, and else. Alternatively, the memory circuit 10 may include portable media such as a universal serial bus (USB) memory and a digital video disk (DVD).

The memory circuit 10 stores therein a variety of processing programs (including application programs and an operating system (OS)) for use in the processing circuitry 11, data necessary for execution of the programs, volume data, and medical images. The OS can incorporate a graphical user interface (GUI) that graphically presents information to the operator on the display 14 and allows the operator to perform basic operations with the input I/F circuit 12.

The processing circuitry 11 serves as a processor that implements intended functions by reading and executing the corresponding programs from the memory circuit 10. The processing circuitry 11 includes, for instance, an acquiring function 11a, a dividing function 11b, an extracting function 11c, and an output control function 1id. The processing circuitry 11 reads various control programs from the memory circuit 10 to implement the acquiring function 11a, the dividing function 11b, the extracting function 11c, and the output control function 11d as well as to collectively control the operations of the memory circuit 10, the input I/F circuit 12, the communication I/F circuit 13, and the display 14. In other words, the processing circuitry 11 has the respective functions illustrated in FIG. 3 as a result of reading the control programs.

Referring to FIG. 3, the acquiring function 11a, the dividing function 11b, the extracting function 11c, and the output control function 11d are implemented by a single processor, i.e., the processing circuitry 11, by way of example. Alternatively, the processing circuitry can be configured by combining two or more independent processors so that the processors individually execute the programs to implement the corresponding functions. In addition, referring to FIG. 3, the single memory circuit 10 stores the programs corresponding to the functions, by way of example. Alternatively, two or more memory circuits 10 may be provided in a distributed manner to allow the processing circuitry 11 to read the programs from the individual memory circuits 10.

The term "processor" used as above signifies circuitry such as a central processing unit (CPU), a graphics processing unit (GPU), an application specific integrated circuit (ASIC), a programmable logic device (e.g., a simple programmable logic device (SPLD) or a complex programmable logic device (CPLD)), and a field programmable gate array (FPGA). The processor serves to implement the functions by reading and executing the programs from the memory circuit 10. The programs may be directly incorporated in the circuitry of the processor, instead of being stored in the memory circuit 10. In such a case the processor reads and executes the programs from its own circuitry to implement the functions.

The acquiring function 11a serves to acquire medical image data representing a region containing a target site from the medical image diagnosis apparatus 2 and the medical image server 3 via the network N. Specifically, the acquiring function 11a acquires medical image data representing the head of a subject captured by the medical image diagnosis apparatus 2, from the medical image diagnosis apparatus 2 and the medical image server 3. In the present embodiment the medical image data is defined as cerebral artery mask image data representing the cerebral arteries as a region of interest, which is created by subtraction from contrast image data and non-contrast image data of the brain.

The dividing function 11b serves to create a plurality of pieces of divisional image data (divisional data) of the cerebral arteries being a target site by dividing the cerebral artery mask image data, acquired by the acquiring function 11a, according to, for example, an anatomical structure.

Specifically, the cerebral arteries can be divided into the anterior circulation from the internal carotid arteries each of which bifurcates into the anterior cerebral artery and the middle cerebral artery, and the posterior circulation from the basilar artery which bifurcates into the posterior cerebral arteries. In accordance with this anatomical structure, the dividing function 11b divides the cerebral artery mask image data into anterior circulation mask image data and posterior circulation mask image data with reference to, for example, the positions of the posterior communicating arteries P-corn. The anterior circulation mask image data and the posterior circulation mask image data are exemplary divisional data. The anterior circulation mask image data is exemplary anterior circulation image data. The posterior circulation mask image data is exemplary posterior circulation image data.

Figure 4:
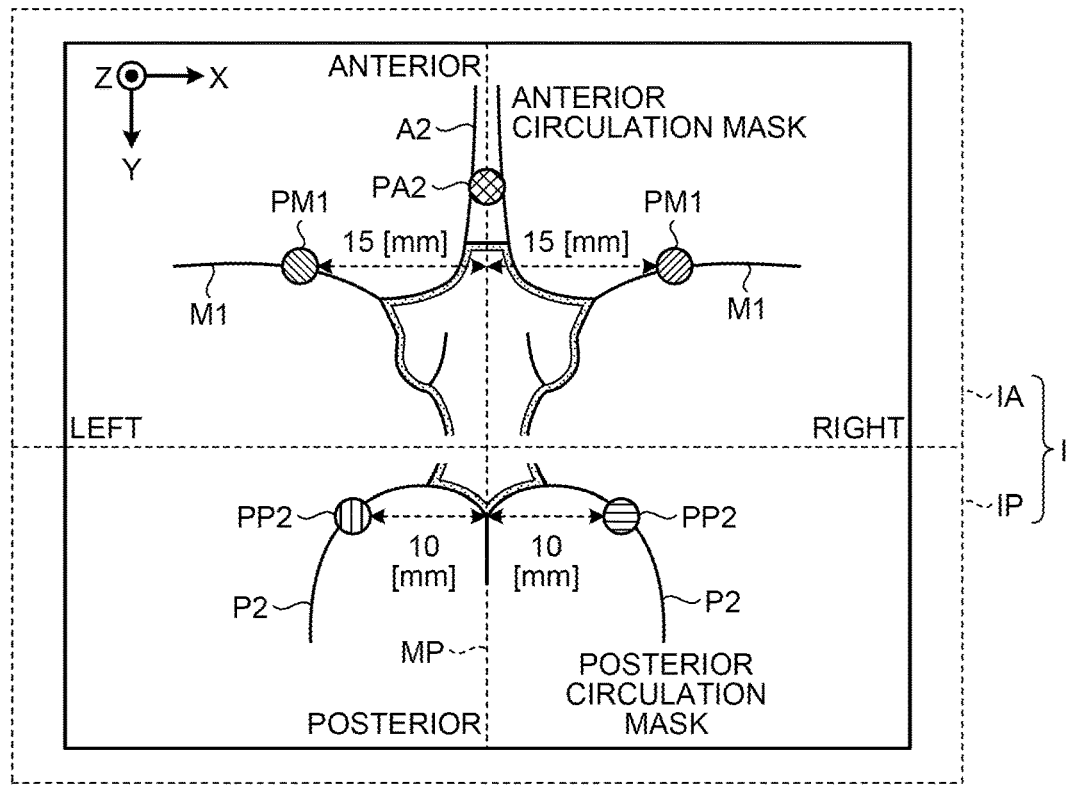
FIG. 4 illustrates a cerebral artery mask image divided into an anterior circulation mask image and a posterior circulation mask image by a divisional function.

FIG. 4 illustrates an example of the cerebral artery mask image I divided into an anterior circulation mask image IA and a posterior circulation mask image IP by the dividing function 11b, as viewed from above the head. As illustrated in FIG. 4, the cerebral artery mask image I is divided such that the anterior circulation mask image IA and the posterior circulation mask image IP both depict part of the circle of Willis with the left and right maximal-length structures in the left and right sides of the brain in a manner to maintain continuity thereof. Thus, the image of part of the circle of Willis is, for example, divided so as to include a characteristic portion of the anterior circulation, i.e., the left and right maximal-length structures of the middle cerebral artery and to maintain the continuity of the left and right sides of the middle cerebral artery.

In the present embodiment the cerebral blood vessels appearing on the anterior circulation mask image are referred to as an anterior circulation mask. The cerebral blood vessels appearing on the posterior circulation mask image are referred to as a posterior circulation mask. The cerebral blood vessels appearing on the cerebral artery mask image data (i.e., cerebral blood vessels including the anterior circulation mask and the posterior circulation mask) are simply referred to as a cerebral artery mask.

The extracting function 11c serves to extract, from each piece of divisional data, a target region corresponding to a target site in accordance with a particular condition. That is, the pieces of divisional data each contain at least part of the target site. The particular condition can be defined for each divisional data on the basis of the anatomical structure of at least part of the target site contained in the divisional data. The extracting function lic extracts the target region corresponding to the target site from each divisional data under the particular condition defined for the divisional data. For example, the extracting function lic extracts a target region corresponding to the circle of Willis being a target site in accordance with the particular condition based on the anatomical structure for each of the anterior circulation mask image and the posterior circulation mask image.

More specifically, the extracting function lic calculates coordinate values of a plurality of characteristic points on each of the anterior circulation mask image and the posterior circulation mask image according to the particular condition based on the anatomical structure. Examples of the characteristic points include characteristic points PM1 in M1 segments of the middle cerebral artery, characteristic points PA2 in A2 segments of the anterior cerebral arteries, and characteristic points PP2 in P2 segments of the posterior cerebral arteries. The characteristic points are calculated, for example, under the following particular conditions:

Characteristic points PM1: located on the anterior circulation mask and 15 mm away rightward and leftward from the median plane MP;

Characteristic points PA2: located at the intersection between the cerebral blood vessel on the anterior circulation mask and the central plane between the axial plane passing the forefront of the anterior circulation mask and the axial plane passing one of the left and right characteristic points PM1, the one being lower in position; and Characteristic points PP2: located on the posterior circulation mask and 10 mm away rightward and leftward from the median plane MP.

Figure 5:
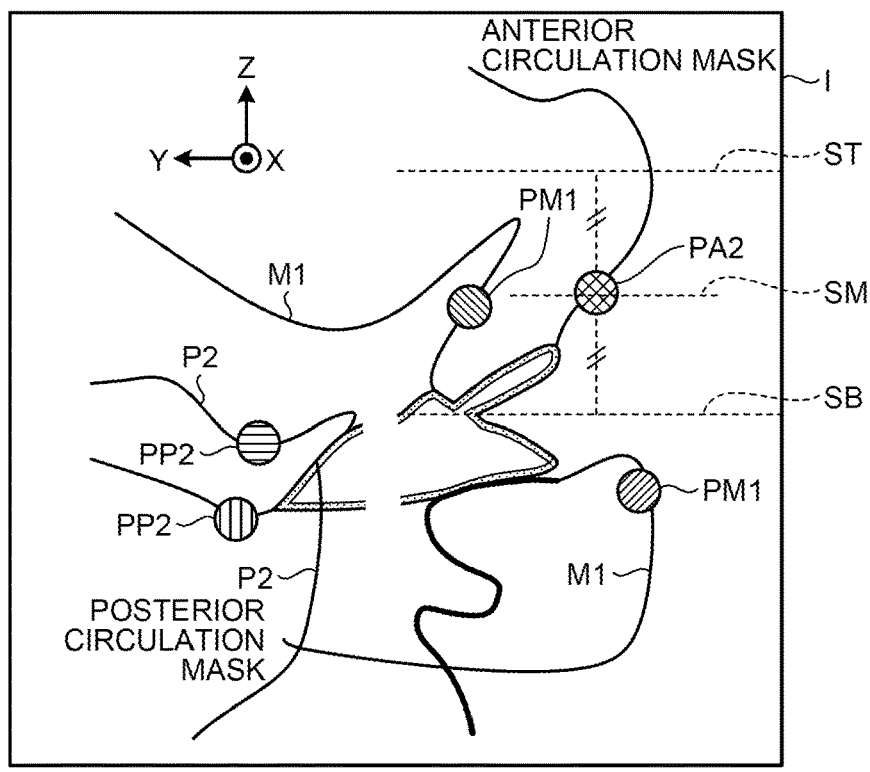
FIG. 5 illustrates the positions of characteristic points on both of the anterior circulation mask image and the posterior circulation mask image.

FIG. 5 illustrates an example of the cerebral artery mask image I of FIG. 4, as viewed from the rightward direction. As illustrated in FIG. 4 and FIG. 5, the left and right characteristic points PM1 are set on the anterior circulation mask and on the left and right M1 segments 15 mm away leftward and rightward from the median plane MP. The left and right characteristic points PM1 set as above correspond to approximately the centers of the M1 segments due to the anatomical structure.

As illustrated in FIG. 4 and FIG. 5, the left and right characteristic points PA2 are set at the intersection between the cerebral blood vessel on the anterior circulation mask and a central plane SM between an axial plane ST passing the forefront of the anterior circulation mask and an axial plane SB passing one of the left and right characteristic points PM1, the one being lower in position. The left and right characteristic points PA2 set as above correspond to approximately the centers of the A2 segments due to the anatomical structure.

As illustrated in FIG. 4 and FIG. 5, the left and right characteristic points PP2 are set on the posterior circulation mask and on the left and right P1 or P2 segments 10 mm away leftward and rightward from the median plane MP. The left and right characteristic points PP2 set as above correspond to approximately the boundaries between the P1 segments and the P2 segments due to the anatomical structure.

The particular conditions as to the characteristic points PM1, PA2, and PP2 are presented for illustrative purpose only. The user can change the particular conditions depending on, for example, individual differences among subjects. An example of the changed condition is such that "located on the anterior circulation mask and 18 mm away from the median plane MP".

The extracting function 11c extracts the circle of Willis from the cerebral artery mask with reference to the characteristic points PM1, PA2, and PP2 set on the anterior circulation mask image and the posterior circulation mask image. Specifically, the extracting function 11c calculates maximal values and minimal values of x-coordinates, y-coordinates, and z-coordinates of the respective characteristic points PM1, PA2, and PP2 on the anterior circulation mask image and the posterior circulation mask image, to calculate a closed region (herein, a cuboid) defined by the maximal values and the minimal value of the respective coordinates. The extracting function 11c extracts, as the circle of Willis, a cerebral artery mask region from the closed region as calculated.

There may be a situation that it is not possible to set at least any of the left and right characteristic points PM1, PA2, and PP2 due to individual differences among subjects or other factors. In such a situation the extracting function 11c interpolates the characteristic point or points in question by characteristic-point interpolation to calculate the respective coordinates thereof.

That is, the extracting function 11c determines whether or not all of the left and right characteristic points PM1, PA2, and PP2 are successfully set on both the anterior circulation mask image and the posterior circulation mask image. After determining a failure in setting any of the left and right characteristic points PM1, PA2, and PP2, the extracting function 11c interpolates the characteristic point in question through the characteristic-point interpolation.

Figure 6:
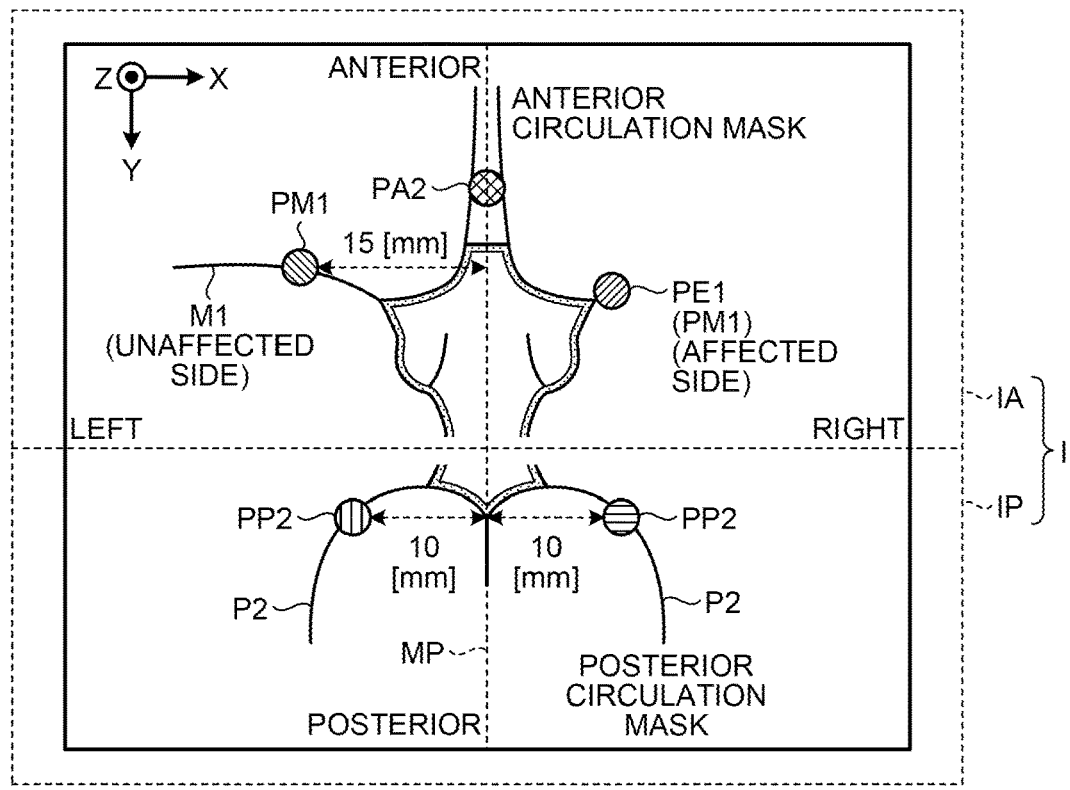
FIG. 6 is an explanatory view for an exemplary characteristic-point interpolation.
Figure 7:
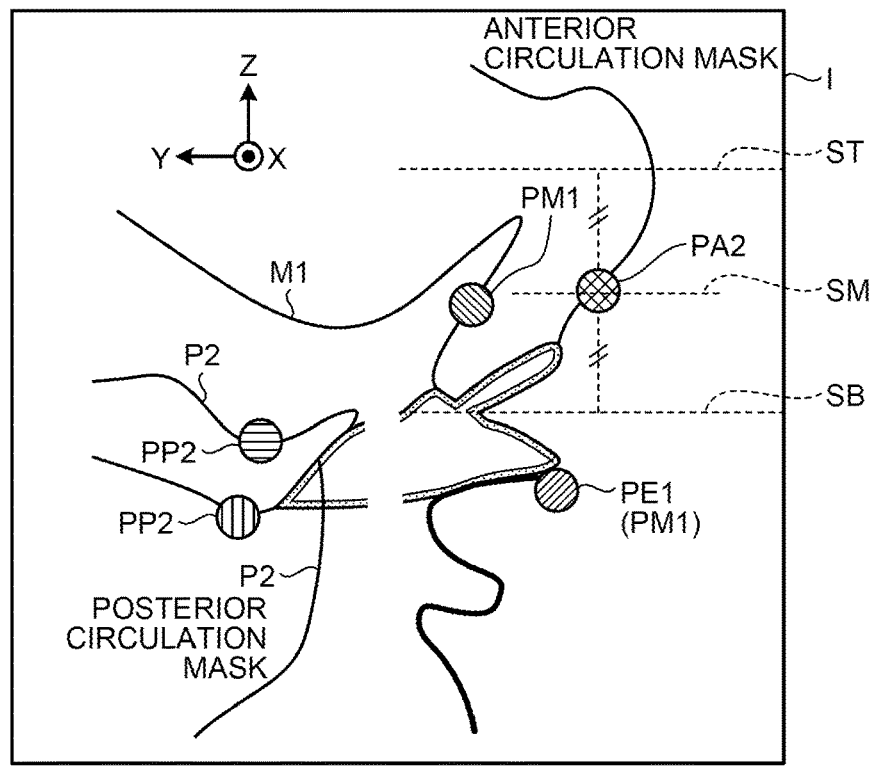
FIG. 7 is another explanatory view of the characteristic-point interpolation.

FIG. 6 and FIG. 7 are explanatory views for the characteristic-point interpolation. In the examples of FIG. 6 and FIG. 7, an occlusion is identified in the M1 segment of the middle cerebral artery on the right side of the patient while no occlusion is identified in the M1 segment of the middle cerebral artery on the left side of the patient. In the present embodiment, the right side of the patient with an occlusion in the M1 segment of the middle cerebral artery is referred to as an affected side. The left side of the patient with no occlusion in the M1 segment of the middle cerebral artery is referred to as an unaffected side.

As illustrated in FIG. 6, the right M1 segment of the middle cerebral artery of the patient in question is insufficient in terms of length because of presence of the occlusion, therefore, setting the right characteristic point PM1 according to the particular condition is not possible.

In such a case the extracting function 11c determines that setting the characteristic point PM1 is not possible so that the number of the characteristic points is inadequate, and sets an end point PE1, as identified on the anterior circulation mask in FIG. 6, as the characteristic point PM1, for example. The extracting function 11c sets the end point PE1 as the characteristic point PM1 on the affected side of the anterior circulation mask, as illustrated in FIG. 6 and FIG. 7. As a result, the extracting function 11c succeeds in setting all of the left and right characteristic points PM1, PA2, and PP2.

In some cases the occlusion may largely spread in the middle cerebral artery, which may prevent identification of the middle cerebral artery as a whole on the affected side of the anterior circulation mask. In such a case the extracting function 11c sets a symmetric point of the characteristic point PM1 on the unaffected side of the anterior circulation mask with respect to the median plane. The extracting function 11c then sets the symmetric point PS1 as the characteristic point PM1 on the affected side of the anterior circulation mask. In this manner, the extracting function 11c succeeds in setting all of the left and right characteristic points PM1, PA2, and PP2.

The extracting function 11c calculates the maximal values and the minimal values of the x-coordinates, y-coordinates, and z-coordinates of the characteristic points PM1, PA2, and PP2 including the ones set by the interpolation, to calculate the closed region defined by the maximal values and the minimal values of the respective coordinates. The extracting function 11c extracts, as the circle of Willis, a cerebral artery mask region from the closed region as calculated.

The output control function 11d serves to perform output control of information on the circle of Willis as extracted. For example, the output control function 11d causes the display 14 to display the image of the extracted circle of Willis. The display 14 may display the positions of the respective characteristic points on the image of the circle of Willis. Alternatively, the display 14 can display two separate windows, that is, one showing the image of the circle of Willis with indication of the positions of the respective characteristic points and the other showing the same with no indication of the positions of the characteristic points.

Further, the output control function lid outputs, to a subsequent-stage clinical application, the coordinate group of the region corresponding to the extracted circle of Willis and the coordinates of the respective characteristic points together with the medical image data such as cerebral artery mask image data or contrast image data and non-contrast image data of the brain used in generation of the cerebral artery mask image. In addition, the output control function 11d can add the coordinate group of the region corresponding to the extracted circle of Willis and the coordinates of the respective characteristic points to the image data as supplementary information conforming to the DICOM standard.

The input I/F circuit 12 is a circuit that receives signals from an input device as a pointing device (for example, a mouse) and/or a keyboard operable by the operator. Herein, the input I/F circuit 12 is considered to include such an input device. In response to an operator's manipulation of the input device, the input I/F circuit 12 generates an input signal in accordance with the manipulation and outputs the signal to the processing circuitry 11. The medical image processing apparatus 1 may be equipped with a touch panel incorporating the input device and the display 14 in a united manner.

The input I/F circuit 12 is implemented, for example, by a trackball, a switch button, a mouse, and a keyboard for setting a region of interest (ROI) and else, a touch pad with a surface that receives user inputs by touch, a touch screen being the assembly of a display screen and a touch pad, a non-contact input circuit including an optical sensor, and a touch panel display being the assembly of an audio input circuit, a display screen, and a touch pad.

The input I/F circuit 12 is not limited to the one including physical operational components such as a mouse and a keyboard. Examples of the input I/F circuit 12 include electric-signal processing circuitry that receives an electric signal corresponding to an input from an external input device independent from the apparatus, and outputs the electric signal to a control circuit.

The communication I/F circuit 13 performs communications with external devices in compliance with a given communication standard. In the medical image processing apparatus 1 installed on the network, the communication interface 13 receives and transmits information from and to external devices on the network. For example, the communication interface 13 receives captured image data from the medical image diagnosis apparatus 2 or the medical image server 3 via the network N.

The display 14 serves as an image display including a liquid crystal display (LCD). In accordance with an instruction from the processing circuitry 11, the display 14 displays various operation screens and various kinds of display information such as image data on the LCD.

Target Site Extraction

The following will describe a target site extraction to be executed by the medical image processing apparatus 1 of the present embodiment.

Figure 8:
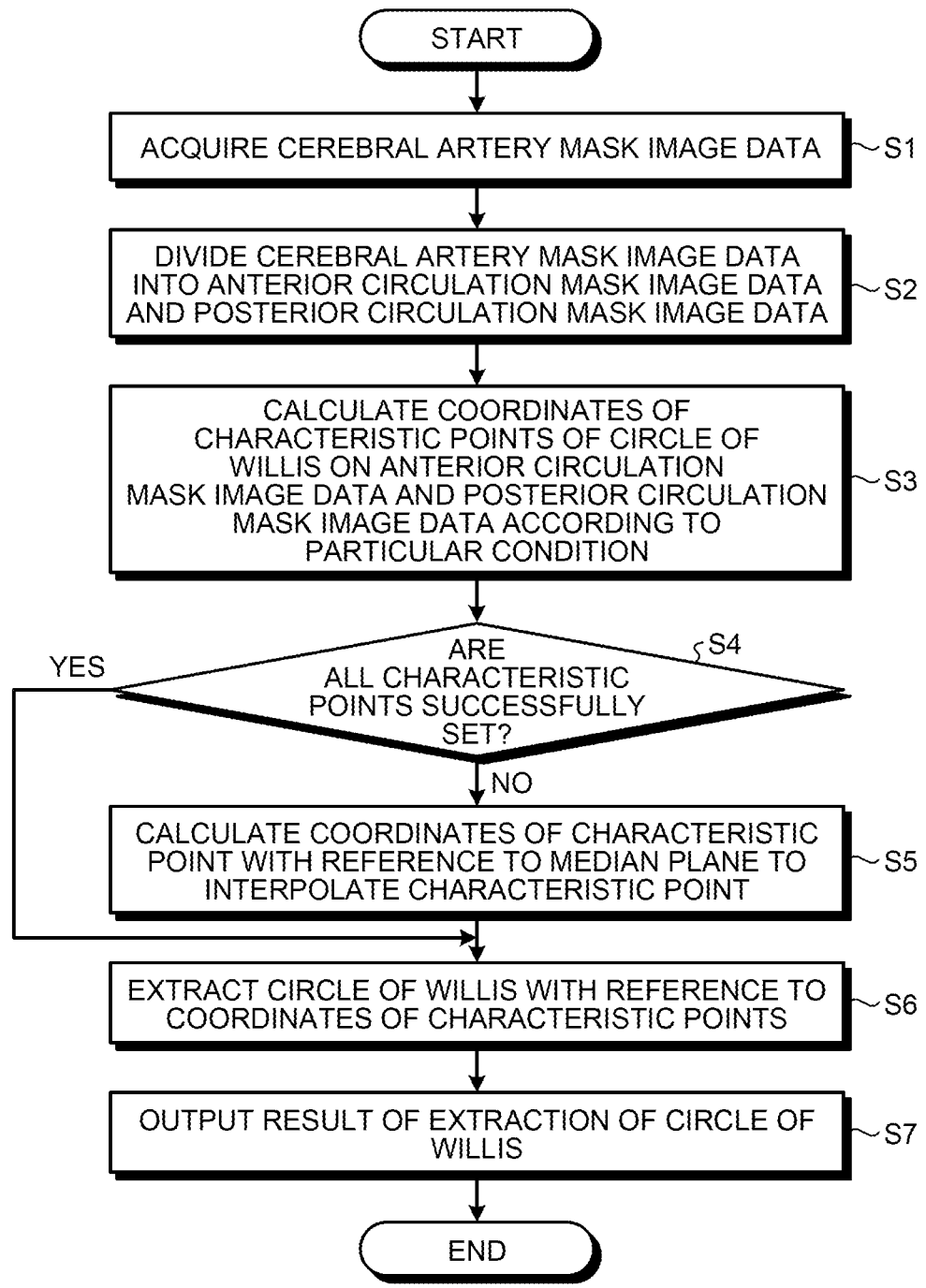
FIG. 8 is a flowchart illustrating an exemplary target site extraction to be executed by the medical image processing apparatus.

FIG. 8 is a flowchart illustrating a process of target site extraction that the medical image processing apparatus 1 executes. As illustrated in FIG. 8, the acquiring function 11a acquires cerebral artery mask image data from the medical image diagnosis apparatus 2 and the medical image server 3 via the network N (step S1). The acquired cerebral artery mask image data is adjusted in position such that the median plane includes the Z-axis.

The dividing function 11b divides the cerebral artery mask image data into anterior circulation mask image data and posterior circulation mask image data according to the anatomical structure (step S2).

The extracting function 11c extracts the circle of Willis as a target region corresponding to a target site from each of the anterior circulation mask image data and the posterior circulation mask image data according to a particular condition based on the anatomical structure (step S3).

The extracting function 11c determines whether all of the characteristic points PM1, PA2, and PP2 are successfully set on both the anterior circulation mask image data and the posterior circulation mask image data (step S4). After determining a failure in setting any of the characteristic points on the anterior circulation mask image data and/or the posterior circulation mask image data (NO in step S4), the extracting function 11c calculates the coordinates of the characteristic point or points in question with reference to the reference plane (i.e., median plane) for interpolation of the characteristic point or points (step S5). After determining that all of the characteristic points PM1, PA2, and PP2 are successfully set on both the anterior circulation mask image data and the posterior circulation mask image data (YES in step S4), the extracting function 11c proceeds to step S6.

The extracting function 11c extracts the circle of Willis from the cerebral artery mask image data with reference to the set characteristic points PM1, PA2, and PP2 on the anterior circulation mask image data and the posterior circulation mask image data (step S6).

The output control function 11d performs output control of information on the circle of Willis as extracted (step S7). For example, the output control function 11d causes the display 14 to display the image of the extracted circle of Willis. Additionally, the display 14 can display the image of the circle of Willis together with indication of the positions of the respective characteristic points. Further, the output control function 11d outputs, to a subsequent-stage clinical application, the coordinate group of the region corresponding to the extracted circle of Willis and the coordinates of the respective characteristic points together with the medical image data such as cerebral artery mask image data or contrast image data and non-contrast image data of the brain used in generation of the cerebral artery mask image.

As described above, the medical image processing apparatus 1 of the present embodiment includes the acquiring function 11a serving as an acquirer, the dividing function 11b serving as a divider, the extracting function 11c serving as an extractor, and the output control function 11d serving as an output controller. The acquiring function 11a serves to acquire medical image data representing a region including a target site. The dividing function 11b serves to divide the medical image data into a plurality of pieces of divisional data according to the anatomical structure. The extracting function 11c serves to extract a target region corresponding to the target site from each of the pieces of divisional data according to a particular condition. The output control function 11d causes the display 14 to display information on the extracted target region.

As an example, the dividing function 11b divides cerebral artery mask image data being medical image data into anterior circulation mask image data and posterior circulation mask image data according to the anatomical structure. The extracting function 11c extracts a target region corresponding to the circle of Willis from each of the anterior circulation mask image data and the posterior circulation mask image data according to the particular condition. The output control function 11d causes a display 14 to display information on the extracted target region.

Consequently, the medical image processing apparatus 1 can set the particular condition for each of the pieces of divisional data to extract the target regions corresponding to the target site according to the individual conditions. Thereby, the medical image processing apparatus 1 can automatically perform region extraction of a target site of various shapes accurately. In particular, it is made possible to provide a region extraction applicable to target sites, such as the circle of Willis, which are sometimes hypoplastic.

Further, the particular conditions can be geometric conditions based on the anatomical structure. The medical image processing apparatus 1 can set a plurality of characteristic points on each of the pieces of divisional data according to the geometric conditions to extract the target region with reference to the characteristic points. The geometric conditions can be optionally changed. The medical image processing apparatus 1 is thus able to implement region extraction of a target site which is various in terms of shape, taking the individual differences in the target site into account.

If failing to set at least one of the characteristic points on each of the pieces of divisional data, the extracting function 11c interpolates the characteristic point or points concerned with reference to the reference plane such as the median plane. In the case of the circle of Willis being a target site, presence of an occlusion in the cerebral artery may hinder setting of any of the characteristic points. However, such a characteristic point can be interpolated by the interpolation. As a result, the medical image processing apparatus 1 can deal with a variety of shapes of target sites arising from disease, disorder, or else. If an occlusion occurs in the artery due to a blood clot, for example, it is not possible to see structures located farther than the occlusion on the arterial mask. Even in such a case, the medical image processing apparatus 1 can automatically and accurately perform a region extraction.

In addition, the output control function 11d causes the display 14 to display the image of the extracted circle of Willis together with indication of the positions of the characteristic points. This enables the observer to recognize according to which characteristic points the circle of Willis is extracted, by viewing the positions of the characteristic points on display. The output control function 11d also allows non-indication of the characteristic points when necessary, which enables the observer to observe the image of the circle of Willis without indication of the characteristic points.

The output control function 11d outputs, to a subsequent-stage clinical application, the coordinate group of the region corresponding to the extracted circle of Willis and the coordinates of the respective characteristic points together with the medical image data such as cerebral artery mask image data or contrast image data and non-contrast image data of the brain used in generation of the cerebral artery mask image. This enables the subsequent-stage clinical application to perform processing using the coordinate group of the region corresponding to the accurately extracted circle of Willis and the coordinates of the respective characteristic points. Consequently, the clinical application can improve the processing in accuracy and efficiency.

First Modification

The above embodiment has described dividing the cerebral artery mask image data according to the anatomical structure to create a plurality of pieces of divisional image data of the cerebral arteries being a target site, by way of example. Alternatively, it is possible to create the pieces of divisional image data of the cerebral arteries by dividing cerebral artery mask image data according to geometric features of a certain site, such as size or length, of the cerebral artery mask, in place of or in addition to the anatomical structure, for example.

Second Modification

The above embodiment has described dividing the cerebral artery mask image data into two pieces of image data, i.e., anterior circulation mask image data and posterior circulation mask image data according to the anatomical structure, by way of example. However, the number of divisions of the cerebral artery mask image data can be set in accordance with intended features to calculate. For instance, after the cerebral artery mask image data is divided into the anterior circulation mask image data and the posterior circulation mask image data, each of the anterior circulation mask image data and the posterior circulation mask image data can be additionally divided into left-brain image data and right-brain image data with reference to the median plane, for example.

Third Modification

The above embodiment has described calculating the coordinates of the characteristic points on the anterior circulation mask image data and the posterior circulation mask image data according to their respective particular conditions, by way of example. The particular conditions can include features related to a pixel value such as a pixel value or a variation in the pixel value, in addition to geometric features based on the anatomical structure, such as length or size. Thus, the particular conditions may be individually defined to be a combination of the geometric features and the features related to the pixel value and applied for the pieces of divisional data.

Fourth Modification

The above embodiment has described setting the closed region with reference to the maximal values and the minimal values of the respective coordinate values of the characteristic points PM1, PA2, and PP2 calculated on the anterior circulation mask image data and the posterior circulation mask image data, to extract the circle of Willis from the set closed region, by way of example. Additionally, the set closed region can be adjusted in size in accordance with the structure of the cerebral artery mask within the set closed region.

For example, it is possible to adjust the size of the closed region by uniformly narrowing or expanding the closed region so as not to lose its continuity.

Moreover, the above embodiment has described the closed region of a cuboid form defined by the maximal values and the minimal values of the coordinate values of the characteristic points PM1, PA2, and PP2, by way of example. However, the cuboid form is presented for illustrative purpose only and the closed region can have any form as long as the circle of Willis is extractable from the closed region. As an example, a cuboid region is first set with reference to the maximal values and the minimal values of the coordinate values of the characteristic points PM1, PA2, and PP2, to make a circle having the center at the intersection between the diagonal lines of the cuboid region and having the diameter matching the length of the diagonal lines, and define the circle as the closed region. The circle of Willis can be extracted from the circle.

Fifth Modification

The above embodiment has described, as an example, calculating the maximal values and the minimal values of the x-coordinates, y-coordinates, and z-coordinates of the left and right characteristic points PM1, PA2, and PP2 to calculate the closed region defined by the maximal values and the minimal values of the coordinates, irrespective of execution or non-execution of the characteristic-point interpolation. The cerebral artery mask region is then extracted from the calculated closed region as the circle of Willis.

Alternatively, after execution of the characteristic-point interpolation to a characteristic point on the affected side, the closed region can be set according to a different criterion to extract the circle of Willis therefrom.

Figure 9:
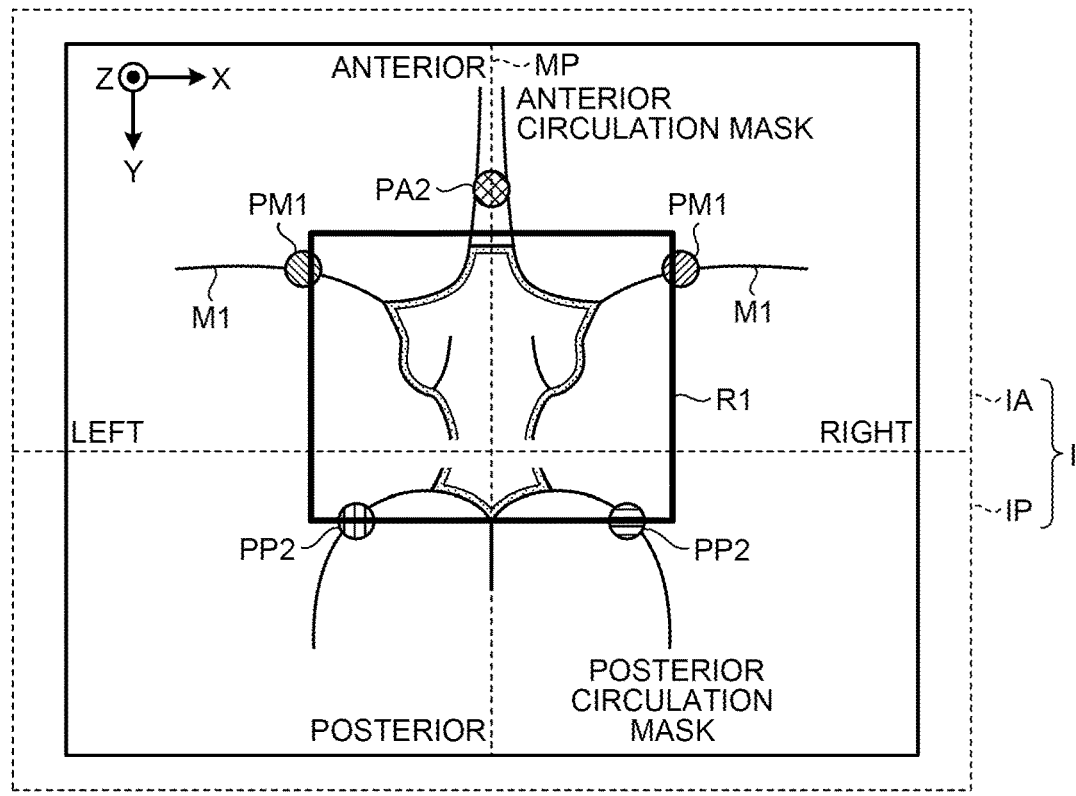
FIG. 9 is an explanatory view for setting a closed region according to a different criterion after execution of the characteristic-point interpolation.
Figure 10:
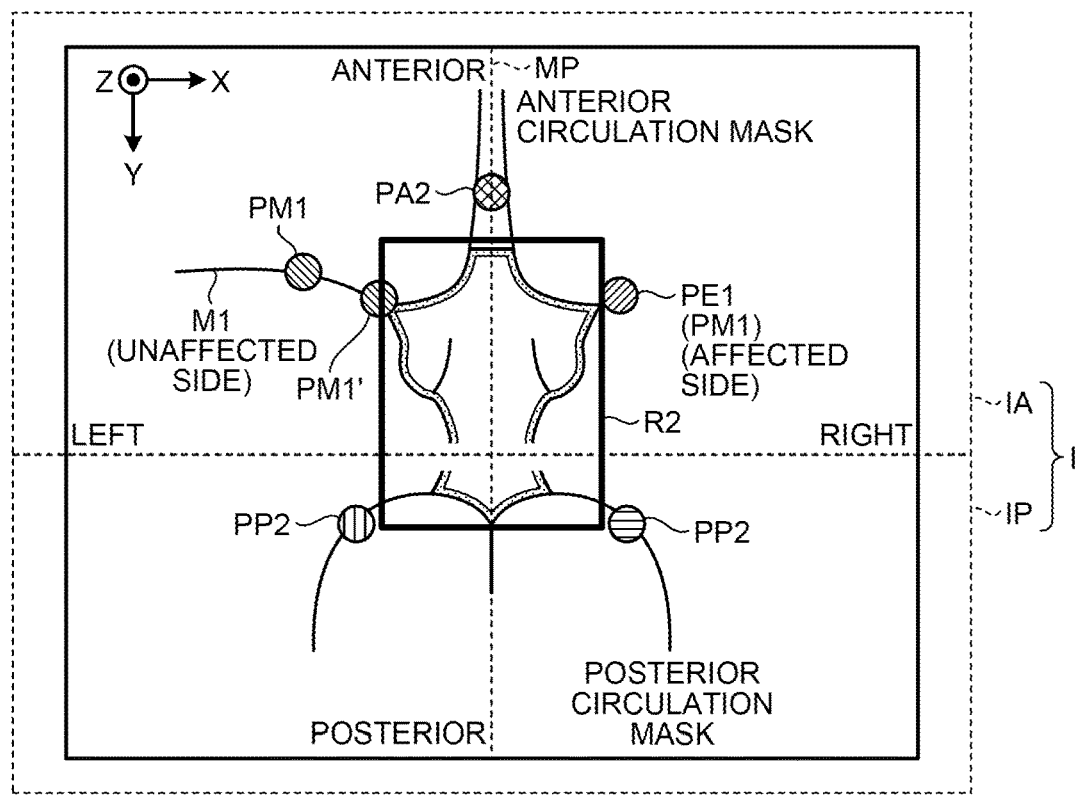
FIG. 10 is an explanatory view for setting a closed region according to a different criterion after execution of the characteristic-point interpolation.

FIG. 9 and FIG. 10 are explanatory views for setting the closed region according to a different criterion after execution of the characteristic-point interpolation. With absence of occlusion in the cerebral arteries (that is, the patient is a normal subject), for example, the characteristic points can be set without interpolation of any characteristic point by the characteristic-point interpolation, as illustrated in FIG. 9. In such a case a closed region R1 is defined by the maximal values and the minimal values of the x-coordinates, y-coordinates, and z-coordinates of the set left and right characteristic points PM1, PA2, and PP2.

Meanwhile, with presence of an occlusion in the M1 segment of the middle cerebral artery, for example, the characteristic point PM1 is interpolated to a characteristic point PE1 at the end of the affected side through the characteristic-point interpolation, and the characteristic point PE1 is set as characteristic point PM1, as illustrated in FIG. 10. After execution of such a characteristic-point interpolation, a characteristic point PM1', symmetric to the characteristic point PE1 on the affected side with respect to the median plane MP, is additionally set on the unaffected side. The maximal values and the minimal values of the x-coordinates, y-coordinates, and z-coordinates of the left and right characteristic points PE1, PM1', PA2, and PP2 are calculated to define a closed region R2 by the maximal values and the minimal values.

In this manner a transversely narrowed closed region can be set with reference to the characteristic points PE1 and PM1' interpolated by the characteristic-point interpolation.

Sixth Modification

The above embodiment has described the circle of Willis as a target site subjected to a target site extraction, by way of example. However, the target site extraction described above is also applicable to other sites than the circle of Willis.

As an example, assume that the heart be a target site. In this case the medical image of the heart is divided into four pieces of divisional data representing the left ventricle, the right ventricle, the left atrium, and the right atrium, respectively. On each of the four pieces of divisional data, a plurality of characteristic points is set according to a particular condition, that is, a geometric condition based on the anatomical structure. A target region, e.g., mitral valve, tricuspid valve, or cardiac chamber, is extracted from each divisional data with reference to the characteristic points, to be able to perform blood flow analysis of the target region, for example.

As another example, assume that the pelvis be a target site. In this case the medical image of the pelvis is divided into three pieces of divisional data representing the innominate bone and the left and right sacral bones, respectively. On each of the three pieces of divisional data, a plurality of characteristic points is set according to a particular condition, that is, a geometric condition based on the anatomical structure. A target region is extracted from each divisional data with reference to the characteristic points, to be able to classify types of pelvic ring injuries in the target region, for example.

Seventh Modification

The above embodiment has described that the medical image processing apparatus 1 and the medical image diagnosis apparatus 2 are independent from each other, by way of example. Alternatively, the medical image diagnosis apparatus 2 may incorporate the medical image processing apparatus 1 in a united manner and the medical image diagnosis apparatus 2 may function as the medical image processing apparatus 1.

Eighth Modification

The above embodiment has described that the medical image diagnosis apparatus 2 is exemplified by an X-ray diagnosis apparatus. Alternatively, the medical image diagnosis apparatus 2 may be a different kind of imaging apparatus such as an X-ray computed tomography imaging apparatus, a magnetic resonance imaging apparatus (e.g., MR-angiography), an ultrasound diagnostic apparatus, a positron emission tomography (PET), or a single photon emission computed tomography (SPECT).

The medical image processing apparatuses and the medical image processing methods presented in the above embodiment and the first to eighth modifications can be implemented by a computer program. In such a case the computer program causes a computer to acquire medical image data representing a region including a target site, divide the medical image data into a plurality of pieces of divisional data according to an anatomical structure, extract a target region corresponding to the target site from each of the pieces of divisional data according to a particular condition, and output information on the extracted target region.

According to at least one of the above-described embodiments, it is made possible to provide a medical image segmentation method applicable to a variety of shapes of sites.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus, comprising processing circuitry configured to:
   acquire medical image data representing a region including a target region;
   divide the medical image data into a plurality of divided regions with respect to a reference plane according to an anatomical structure;
   set a plurality of characteristic points with reference to distances from the reference plane;
   extract the target region based on the plurality of characteristic points; and
   cause an output circuit to output information on the extracted target region,
   wherein
   the processing circuitry is further configured to divide the medical image data such that an anterior circulation mask image data and a posterior circulation mask image data both depict part of a circle of Willis with left and right maximal-length structures in the left and right sides of a brain in a manner to maintain continuity of left and right sides of the circle of Willis.

2. The medical image processing apparatus according to claim 1, wherein
   the processing circuitry is further configured to set the plurality of characteristic points according to a geometric condition based on the anatomical structure.

3. The medical image processing apparatus according to claim 2, wherein the processing circuitry is further configured to:
   set the reference plane on each of the plurality of divided regions, and
   set the plurality of characteristic points according to the particular condition based on a distance from the reference plane.

4. The medical image processing apparatus according to claim 3, wherein
   the processing circuitry is further configured to set the plurality of characteristic points on each of the plurality of divided regions according to the geometric condition based on at least one of a pixel value and a variation in the pixel value.

5. The medical image processing apparatus according to claim 3, wherein the processing circuitry is further configured to:
   set a closed region on the medical image data with reference to the plurality of characteristic points, and
   extract the target region from the closed region.

6. The medical image processing apparatus according to claim 3, wherein
   the processing circuitry is further configured to interpolate, after failing to set at least one of the plurality of characteristic points on each of the plurality of divided regions, the at least one of the plurality of characteristic points with reference to the reference plane.

7. The medical image processing apparatus according to claim 6, wherein
   the processing circuitry is further configured to set a closed region with reference to the at least one of the plurality of characteristic points interpolated with reference to the reference plane.

8. A medical image processing apparatus, comprising processing circuitry configured to:
   acquire medical image data representing a region including a target region;
   divide the medical image data into a plurality of divided regions with respect to a reference plane according to the anatomical structure,
   set a plurality of characteristic points with reference to distances from the reference plane;
   extract the target region based on the plurality of characteristic points; and
   cause an output interface to output information on the extracted target region,
   wherein
   the processing circuitry is further configured to divide the medical image data such that an anterior circulation mask image data and a posterior circulation mask image data both depict part of a circle of Willis with left and right maximal-length structures in the left and right sides of a brain in a manner to maintain continuity of left and right sides of the circle of Willis.

9. The medical image processing apparatus according to claim 8, wherein
   the particular condition includes a geometric condition based on the anatomical structure, and
   the processing circuitry is further configured to set the plurality of characteristic points on each of the plurality of divided regions according to a geometric condition to extract the target region with reference to the plurality of characteristic points.

10. The medical image processing apparatus according to claim 9, wherein the processing circuitry is further configured to:
    set a median plane on each of the plurality of divided regions, and
    set the plurality of characteristic points according to the particular condition based on a distance from the median plane.

11. The medical image processing apparatus according to claim 10, wherein the processing circuitry is further configured to:
    set a closed region on the medical image data with reference to the plurality of characteristic points, and
    extract the target region from the closed region.

12. The medical image processing apparatus according to claim 11, wherein
the processing circuitry is further configured to interpolate, after failing to set at least one of the plurality of characteristic points on each of the plurality of divided regions, the at least one of the plurality of characteristic points with reference to the median plane.

13. The medical image processing apparatus according to claim 12, wherein
the processing circuitry is further configured to set the closed region with reference to the at least one of the plurality of characteristic points interpolated with reference to the median plane.

14. The medical image processing apparatus according to claim 9, wherein
the processing circuitry is further configured to set the plurality of characteristic points on each of the plurality of divided regions according to the particular condition based on at least one of a pixel value and a variation in the pixel value.

15. The medical image processing apparatus according to claim 1, wherein
the processing circuitry is further configured to cause the output circuit to output at least coordinate information on the target region and coordinate information on the plurality of characteristic points.

16. The medical image processing apparatus according to claim 2, wherein
the processing circuitry is further configured to cause the output interface to display an image representing the target region together with indication of the plurality of characteristic points.

17. A medical image processing method, comprising:
acquiring medical image data representing a region including a target region;
dividing the medical image data into a plurality of divided regions with respect to a reference plane according to an anatomical structure;
setting a plurality of characteristic points with reference to distances from the reference plane;
extracting the target region based on the plurality of characteristic points; and
outputting information on the extracted target region,
wherein
in the dividing, the medical image data is divided such that an anterior circulation mask image data and a posterior circulation mask image data both depict part of a circle of Willis with left and right maximal-length structures in the left and right sides of a brain in a manner to maintain continuity of left and right sides of the circle of Willis.

18. A medical image processing apparatus, comprising processing circuitry configured to:
acquire medical image data representing a region including a circle of Willis;
divide the medical image data into anterior circulation image data and posterior circulation image data according to anatomical structure, the medical image data being such that anterior circulation mask image data and posterior circulation mask image data both depict part of the circle of Willis with left and right maximal-length structures in the left and right sides of the brain in a manner to maintain continuity of left and right sides of the circle of Willis;
extract a target region corresponding to the circle of Willis from each of the anterior circulation image data and the posterior circulation image data according to a geometric condition based on an anatomical structure; and
cause an output interface to output information on the extracted target region.

19. A medical image processing method, comprising:
acquire medical image data representing a region including a circle of Willis;
divide the medical image data into anterior circulation image data and posterior circulation image data according to anatomical structure, the medical image data being such that anterior circulation mask image data and posterior circulation mask image data both depict part of the circle of Willis with left and right maximal-length structures in the left and right sides of the brain in a manner to maintain continuity of left and right sides of the circle of Willis;
extract a target region corresponding to the circle of Willis from each of the anterior circulation image data and the posterior circulation image data according to a geometric condition based on an anatomical structure; and
cause an output interface to output information on the extracted target region.

* * * * *